(12) United States Patent
Bax et al.

(10) Patent No.: US 8,595,882 B2
(45) Date of Patent: Dec. 3, 2013

(54) POWER TOOTHBRUSH WITH ACTUATOR IN THE BRUSHHEAD

(75) Inventors: Pieter Johannes Bax, Drachten (NL); Johannes Hotze Bernhard De Vries, Haren (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/513,960

(22) PCT Filed: Nov. 22, 2010

(86) PCT No.: PCT/IB2010/055348
§ 371 (c)(1),
(2), (4) Date: Jun. 5, 2012

(87) PCT Pub. No.: WO2011/077289
PCT Pub. Date: Jun. 30, 2011

(65) Prior Publication Data
US 2012/0272464 A1    Nov. 1, 2012

Related U.S. Application Data

(60) Provisional application No. 61/289,500, filed on Dec. 23, 2009.

(51) Int. Cl.
*A46B 13/02* (2006.01)
*A61C 17/34* (2006.01)

(52) U.S. Cl.
USPC ............................................. 15/22.1; 15/22.2

(58) Field of Classification Search
USPC ........................... 15/22.1, 22.2; 601/136, 142
See application file for complete search history.

(56) References Cited

U.S. PATENT DOCUMENTS

| 4,845,795 | A | 7/1989 | Crawford et al. |
| 5,189,751 | A | 3/1993 | Giuliani et al. |
| 5,274,870 | A * | 1/1994 | Stollman ........................ 15/22.1 |
| 6,421,865 | B1 | 7/2002 | McDougall |
| 6,785,929 | B2 | 9/2004 | Fritsch et al. |
| 2005/0127759 | A1 | 6/2005 | Kraus et al. |
| 2007/0145832 | A1 * | 6/2007 | Shimizu et al. ................. 310/15 |

FOREIGN PATENT DOCUMENTS

| DE | 102005009963 A1 | 2/2007 |
| DE | 202007014284 U1 | 3/2008 |
| EP | 1376833 A1 | 1/2004 |
| WO | 2007017823 A1 | 2/2007 |
| WO | 2007020599 A2 | 2/2007 |

* cited by examiner

*Primary Examiner* — Randall Chin

(57) ABSTRACT

A power toothbrush includes a small electromagnetic actuator positioned within the brushhead for driving a brushhead assembly which includes a brushhead portion with bristles extending therefrom. The actuator includes a fixed lower element and a moveable upper element, with the lower and upper elements each having curved roller contacting portions at opposing ends thereof. Roller members are positioned between the roller contacting portions of the upper and lower members. At least one coil is mounted on the lower element, responsive to an alternating current energizing signal. Further, at least two permanent magnet assemblies are positioned on the upper element, having alternating polarity positions.

17 Claims, 2 Drawing Sheets

POWER TOOTHBRUSH WITH ACTUATOR IN THE BRUSHHEAD

This application is a national stage application under 35 U.S.C. §371 of International Application No. PCT/IB2010/055348 filed on Nov. 22, 2010, which claims priority to U.S. Provisional Application No. 61/289,500 filed on Dec. 23, 2009.

This invention relates generally to power toothbrushes, and more particularly to a power toothbrush using an electromagnetic actuator assembly, configured and arranged to be positionable in the brushhead of the toothbrush or useful in other personal care appliance arrangements.

Power toothbrushes are generally larger and heavier than corresponding manual toothbrushes, typically due to the size and weight of the driver mechanism for the brushhead, as well as the battery providing the power for the driver. Manual toothbrushes, due to their small size and relatively light weight, are convenient to use, particularly in portable use, since they are readily transportable in a purse, briefcase or the like, as well as being easy to manipulate during actual physical use. They are also generally less expensive than power toothbrushes. However, manual toothbrushes are generally significantly less effective in cleaning teeth than power toothbrushes.

Hence, it is desirable to have a power toothbrush which is comparable in cleaning effectiveness with other power toothbrushes, but is significantly smaller and lighter than typical power toothbrushes, coming close to the size and weight of a conventional manual toothbrush.

Accordingly, the power toothbrush comprises: a handle; a brushhead assembly, including a brushhead member with bristles extending therefrom; a brushhead assembly actuator which comprises a spring mass system including a non-moving stator lower member and a moving upper member, the upper and lower members including spaced curved portions which are in registry; two roller members, each roller member captured between a curved portion of the upper member and the lower member; and a driving assembly for moving the upper member back and forth on the roller members, producing an oscillating action of the brushhead assembly and the bristles for cleaning of the teeth.

As mentioned above, power toothbrushes are generally effective in cleaning teeth. In one example, the power toothbrush shown in U.S. Pat. No. 5,189,751 uses an electromagnetic actuator and operates in the sonic frequency range of approximately 150-400 Hz. The toothbrush of the present invention, shown in FIGS. 1 and 2, also uses an electromagnetic actuator, and has an operating frequency in the range of 190-260 Hz. The actuator assembly for the toothbrush of FIG. 1 is structured such that it is capable of being located in a brushhead portion of the power toothbrush, permitting the handle portion thereof to more resemble the size and weight of a manual toothbrush.

Figure 1:
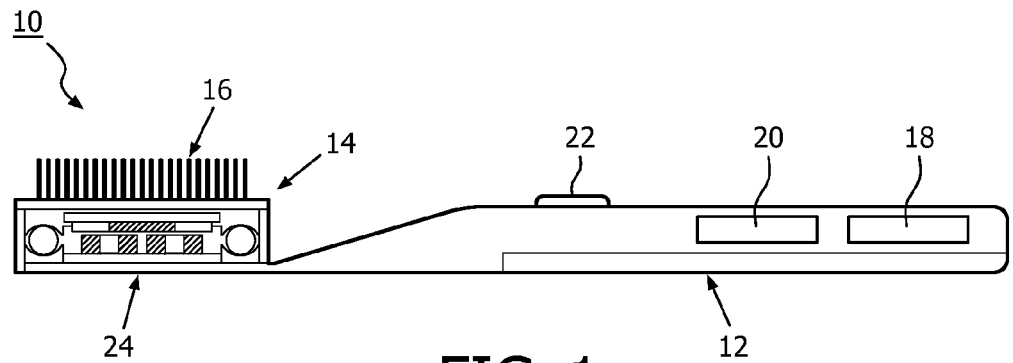
FIG. 1 is a longitudinal cross-sectional view of an embodiment of the power toothbrush which is the subject of this application.
Figure 2:
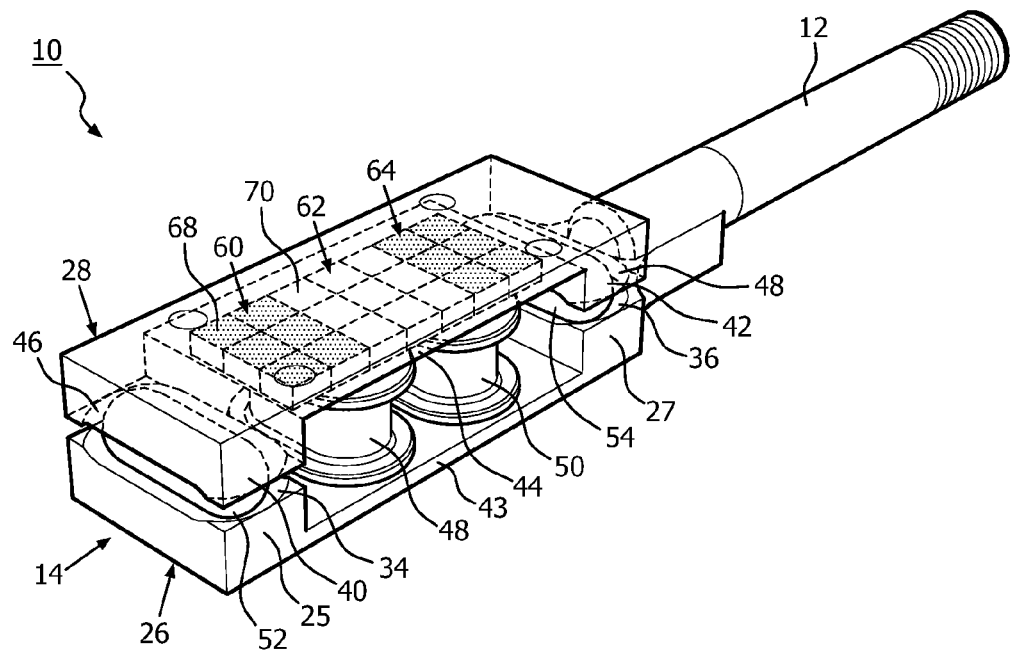
FIG. 2 is a perspective view of the power toothbrush of FIG. 1, showing the brushhead portion thereof, with an actuator assembly.

The power toothbrush referred to generally at 10 in FIGS. 1 and 2 includes a handle portion 12 and a brushhead portion 14. Mounted on the brushhead 14 is a set of conventional bristles 16 for cleaning of the teeth. In the handle 12, as with other power toothbrushes, are located a battery 18, a microprocessor controller 20 and an on/off switch 22, as well as other elements conventional in a power toothbrush, such as a timer, etc. An electromagnetic actuator, referred to generally at 24 in FIG. 1, is positioned within brushhead 14. Electrical connections (not shown) extend between battery 18 and microprocessor 20 in the handle and actuator 24 in conventional fashion. While actuator 24 is shown positioned in brushhead 14, it could be positioned in the handle, driving the brushhead 14 with the bristles through an electrical connecting element.

Figure 3:
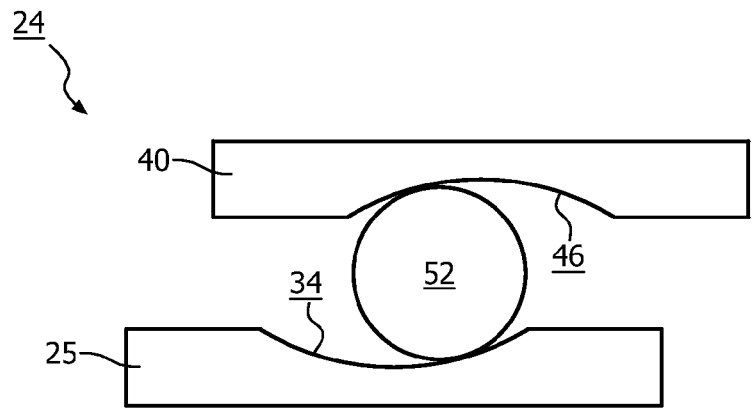
FIG. 3 is a side elevational view of a portion of the actuator assembly shown in FIG. 2.

Actuator 24 is shown in more detail in FIGS. 2 and 3. Actuator 24 includes lower and upper elements 26 and 28. Lower element 26 is fixed in position and functions as the stator portion of the actuator. In the embodiment shown the lower element is a single piece of steel, approximately the size of a typical brushhead. Positioned at each end of the lower element are raised roller support portions 25, 27 which each have a curved portion, referred to at 34 and 36, respectively. The configuration of the curvature of the curved portions 34, 36 at the upper surface of the support portions 25, 27 is discussed in more detail below. Intermediate of and connecting the two raised support portions of the lower element is a plate portion 43.

Upper element 28 is identical to lower element 26 in size and configuration but is positioned so that it is a mirror image of lower element 26. Upper element 28 includes two downwardly facing roller support portions 40 and 42, with an intermediate plate portion 44 therebetween. Support portions 40 and 42, respectively, include curved portions 46 and 48, which face downwardly. Typically, there will be a flexible seal, such as rubber, between the lower element (stator) and the upper element. The seal can be fixed to the lower and upper elements by various means, including gluing, welding and over molding, among others.

Captured between curved portions 34 and 46 at a distal end of the actuator is a first roller 52, while captured between curved portions 36 and 48 at the proximal end of the actuator is a second roller 54. In the embodiment shown, rollers 52 and 54 are made of metal, such as steel, or they can be made of plastic as well. In the embodiment shown, they are typically slightly shorter than the width of upper and lower elements 26 and 28.

Mounted on intermediate plate 43 of the lower element are two coils, 48, 50, each of which has a magnetizable core, such as iron. The coils are wound in the opposite direction. In the embodiment shown, each coil has 64 turns, and is slightly oval in shape, approximately 6 mm wide and 8.5 mm long, although these dimensions and the coil configuration can vary. Although two coils are shown, it is possible to use a single coil, or more coils, e.g. four coils.

Positioned on the intermediate plate 44 of the upper element in the embodiment shown for two coils are three permanent magnet assemblies 60, 62 and 64. The number of permanent magnet assemblies will depend on the number of coils, since each coil should face a north/south separation line of adjacent permanent magnet assemblies. In one particular embodiment, the permanent magnet assemblies 60 and 64 each comprise a total of 6 individual magnets 68-68, arranged three deep laterally of the brushhead and two in the longitudinal direction of the brushhead. In this particular embodiment, each permanent magnet 68 is 2 mm square by 1 mm high. It should be understood, however, that the size of the individual magnets can vary significantly.

The individual magnets are oriented so that the south poles of the permanent magnets 68-68 in permanent magnet assemblies 60 and 64 are facing downwardly (toward the lower element), while the opposing poles face away from the lower element. The intermediate magnet assembly 62 is positioned between and abuts permanent magnet assemblies 60 and 64. The two coils 48 and 50 are positioned so that one coil faces the line of abutment (separation) between permanent magnet assemblies 60 and 62 and the other coil faces the line of abutment between permanent magnet assemblies 62 and 64. If additional coils are used, additional permanent magnet assemblies are necessary. In the particular embodiment shown, permanent magnet assembly 62 comprises a total of nine individual permanent magnets 70-70, three across laterally of the brushhead and three in the longitudinal direction of the brushhead, although four magnets in the longitudinal direction may be preferred. Each magnet in the magnet assembly 62 shown is 2 mm square by 1 mm thick. Again, however, the size of the magnets is simply illustrative. Various sizes of magnets can be used. Permanent magnet assembly 62 is oriented with the north poles of the individual magnets (or magnet) facing the lower element and the south poles facing away from the lower element. While the permanent magnet assemblies described each comprise a plurality of smaller individual permanent magnets, it should be understood that there could be three single permanent magnets forming the permanent magnet assemblies 60, 62 and 64, or other magnet combinations as well.

Actuator 24 operates as a spring mass system with the moving upper element forming the mass, and rollers 52 and 54 are functioning as a spring, even though the rollers do not elongate like a typical spring. This is an advantage over conventional spring mass systems. The curvature of the curved portions 34 and 36 of the raised portions of the lower element and the corresponding curved portions 46 and 48 of the raised portions of the upper element contribute to the spring constant, as well as the magnetic attracting force. The rollers 52 and 54 are circular in cross-section, as shown most clearly in FIG. 3, with a radius of 1½ mm, although this can be varied. The curved portions which bracket each of the rollers each have a curvature which is close to circular near the center of the curved portion, with a radius of 2½ mm at that point, for receiving the 1½ mm radius roller. The same relationship is true for other roller sizes. However, the curvature of the curved portions increasingly flattens out consistently as the curved portions approach their respective opposing ends, where they intersect the flat surface of the upper or lower element.

In general operation, explained in more detail below, the lower element 26 remains fixed in position, while the upper element moves back and forth in reciprocating fashion by electromagnetic action produced by the coils and the permanent magnets. The curved portions of the upper element raised portions roll over the exterior surface of the rollers, with the rollers themselves also moving longitudinally relative to the handle.

In electromagnetic operation, one coil, e.g. coil 48, is wound in one direction, e.g. clockwise, and is responsive to one half of an alternating current energizing signal from the microprocessor resulting in an electromagnetic field which attracts one end of the permanent magnet assembly, thereby moving the upper element. The same current, when applied to the other coil, creates a magnetic field which repels the other end of the permanent magnet assembly, adding to the effect of the first coil.

During the other half of the sinusoidal energizing signal, the magnetic fields from the coils force the permanent magnet assemblies and the upper element in the opposing direction, so that the complete alternating current energizing signal results in a reciprocal back-and-forth action of the upper element on rollers 52 and 54, producing a scrubbing action by the bristles. In the embodiment shown, the frequency of movement is within the range of 190 Hz to 260 Hz.

The relationship between the curved portions of the upper and lower members and the diameter of the roller is important to proper operation of the toothbrush, as indicated above. Typically, the resulting movement of the upper element and the bristles is axial (longitudinal) due to the magnetic interaction between the magnetic field from the energized coils and the permanent magnets. When the upper element moves axially, the rollers themselves roll along the curved portions of the upper and lower elements. Because of the attraction force of the permanent magnets, however, an additional axial force results, attempting to drive the upper element back toward its original longitudinal position, assisting in the axial movement of the upper element and the bristles. By changing the curvature of the rollers, for example elliptical, and the arrangement of the coils and permanent magnets, movement in a direction orthogonal to (and in addition to) axial movement can be realized, resulting in a more complex bristle movement, with more effective cleaning.

In a variation of the above, the rollers could be spherical, which in combination with a particular curvature of the curved portions, could result in an even more complex movement of the brushhead.

Figure 4:
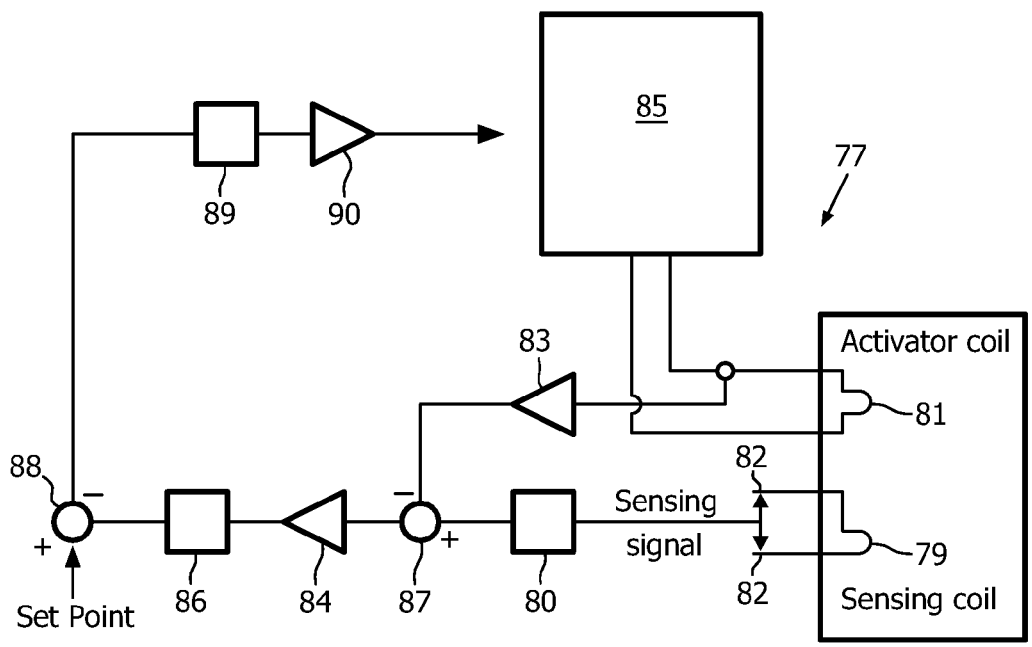
FIG. 4 is a circuit/functional diagram of a power toothbrush which includes an assembly for sensing the operation of the toothbrush.

FIG. 4 shows another feature of the power toothbrush. This feature includes a sensing assembly 77 with a separate sensing coil 79 which is positioned adjacent to the actuator coils. One actuator coil 81 is shown for illustration in FIG. 4. When the upper element moves in operation, the magnetic flux produced by the permanent magnet assemblies (FIG. 2) will produce a voltage across the ends 82-82 of the sensing coil. The voltage signal contains information about the longitudinal movement (stroke) of the upper element, as well as the speed of the back-and-forth movement of the upper element. The voltage across the sensing coil can also contain components produced by the actuator coils, but these can be filtered out, such as with the circuit of FIG. 4.

Referring now to FIG. 4, the signal from the sensing coil 79 is integrated at 80 and compared (87) with the measured current from actuator coil 81, which is energized by a full bridge circuit in the appliance electronics 85 and buffered by buffer 83. The result from comparator 87 is then amplified at 84 and then peak-to-peak detected at 86 to produce stroke information. This value can be used in a normal feedback control system. The value can be compared with a set point value at comparator 88, with the result filtered at 89 to regulate the power output for the full bridge circuit by shifting the frequency or duty cycle at 90 of the feedback control signal to the full bridge. This circuit eliminates the unwanted voltage components present in the signal at 82-82. In use of the appliance, the brushhead is disposable, connected in various ways, e.g. magnetic, mechanical, such as bayonet or slide and click connections, among others. If the actuator is in the handle, connecting brushhead assemblies can be disposable.

Accordingly, a power toothbrush has been disclosed with an actuator which is arranged to provide an oscillating action by an electromagnetic driver. The actuator includes upper and lower elements which include raised portions with curved portions which bracket rollers to provide a spring mass driving action. The invention can be used in other personal care appliances, such as for example shavers, where an end effector for shaving is used.

Although a preferred embodiment has been disclosed for purposes of illustration, it should be understood that various changes and modifications and substitutions could be made in the preferred embodiment without departing from the spirit of the invention as defined by the claims which follow:

The invention claimed is:

1. A power toothbrush with an electromagnetic actuator comprising:
   a handle;
   a brushhead assembly including a brushhead member with bristles extending therefrom;
   a brushhead assembly actuator which includes a lower element having curved contacting portions at spaced locations along a length thereof and an upper element spaced apart from the lower element and having curved contacting portions at spaced locations along a length thereof which are in registry with the curved contacting portions of the lower element;
   at least one actuator coil mounted on the lower element between the curved contacting portions of the lower and upper elements;
   a power assembly for energizing the at least one actuator coil with an alternating current signal;
   at least two permanent magnet assemblies positioned between the curved contacting portions on the upper element, wherein successive permanent magnet assemblies of the at least two permanent magnet assemblies are arranged with successive opposing polarities; and
   roller members captured between the curved contacting portions of the upper and lower elements, wherein the at least one actuator coil and the at least two permanent magnet assemblies are arranged such that an application of an alternating current signal to the at least one actuator coil results in reciprocal movement of the upper element and the brushhead assembly for cleaning of the teeth.

2. The power toothbrush of claim 1, wherein the at least one actuator coil includes two actuator coils mounted on the lower element between the curved contacting portions of the lower element and three permanent magnet assemblies of the at least two permanent magnet assemblies arranged so that two permanent magnet assemblies abut over approximately a centerline of each coil of the two actuator coils.

3. The power toothbrush of claim 1, wherein the curved contacting portions are located at opposing ends of the upper and lower elements and are raised relative to an intermediate portion thereof.

4. The power toothbrush of claim 1, wherein the at least two permanent magnet assemblies include three magnet assemblies that each comprises a plurality of individual magnets.

5. The power toothbrush of claim 1, wherein the at least two permanent magnet assemblies include three permanent magnet assemblies comprising three individual magnets.

6. The power toothbrush of claim 1, wherein the roller members have a circular cross-section, and wherein a center section of the curved contacting portions of at least one of the of the lower and upper elements is approximately circular with a remainder of the contacting curved portions flattening out to opposing ends of the curved contacting portion.

7. The power toothbrush of claim 6, wherein the roller members are approximately 1½ mm in diameter and the center section of the curved contacting portions are approximately 2½ mm in diameter.

8. The power toothbrush of claim 1, wherein the roller members are elongated, extending for approximately a width of the brushhead assembly.

9. The power toothbrush of claim 1, wherein the roller members are spherical.

10. The power toothbrush of claim 1, further comprising a sensing winding assembly, wherein magnetic flux from the at least two permanent magnet assemblies during operation of the power toothbrush produces voltage signals which are indicative of speed and/or stroke of the brushhead member as it moves when the power assembly energizes the actuator coil.

11. The power toothbrush of claim 10, wherein the sensing assembly includes a feedback control circuit for controlling operation of the toothbrush.

12. A power toothbrush, comprising:
   a handle;
   a brushhead assembly including a brushhead member with bristles extending therefrom;
   a brushhead actuator which comprises a spring mass system including a non-moving stator lower member and a moving upper member, the upper and lower members including spaced curved portions which are in registry;
   two roller members, each roller member captured between a curved portion of the upper member and the lower member; and
   a driving assembly for moving the upper member back and forth on the roller members, producing an oscillating action of the brushhead assembly and the bristles for cleaning of teeth.

13. The power toothbrush of claim 12, wherein the driving assembly is an electromagnetic driver responsive to an alternating current drive signal.

14. The power toothbrush of claim 12, wherein a frequency of the oscillating action of the brushhead assembly is in a range of 190-260 Hz.

15. The power toothbrush of claim 12, wherein an exterior of the two roller members is configured relative to curvature of the curved portions of the upper and lower members and permanent magnet assemblies are so arranged relative to coils that the upper member moves longitudinally of the power toothbrush, and toward and away from the lower member.

16. A personal care appliance, comprising:
   a handle;
   a workpiece assembly including an end effector for accomplishing a personal care function;
   a workpiece assembly actuator which comprises a spring mass system including a non-moving stator lower member and a moving upper member, the upper and lower members including space curved portions which are in registry;
   two roller members, each roller member captured between a curved portion of the upper member and the lower member; and
   a driving assembly for moving the upper member back and forth on the roller members, producing an oscillating action of the end effector.

17. The personal care appliance of claim 16, wherein the driving assembly is an electromagnetic driver responsive to an alternating current drive signal.

* * * * *